United States Patent
Yanagisawa

(10) Patent No.: US 7,288,667 B2
(45) Date of Patent: Oct. 30, 2007

(54) PREPARATION OF SULFIDE CHAIN-BEARING ORGANOSILICON COMPOUNDS

(75) Inventor: Hideyoshi Yanagisawa, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 11/529,591

(22) Filed: Sep. 29, 2006

(65) Prior Publication Data

US 2007/0078275 A1   Apr. 5, 2007

(30) Foreign Application Priority Data

Sep. 30, 2005   (JP) .............................. 2005-285848

(51) Int. Cl.
  *C07F 7/04*   (2006.01)
(52) U.S. Cl. .................................... 556/427
(58) Field of Classification Search ...................... None
  See application file for complete search history.

(56) References Cited

U.S. PATENT DOCUMENTS

| 5,405,985 | A | 4/1995 | Parker et al. |
| 5,468,893 | A | 11/1995 | Parker et al. |
| 5,583,245 | A | 12/1996 | Parker et al. |
| 6,384,255 | B1 | 5/2002 | Backer et al. |
| 6,448,426 | B1 | 9/2002 | Backer et al. |
| 2003/0236424 | A1 | 12/2003 | Yanagisawa et al. |

FOREIGN PATENT DOCUMENTS

| JP | 2004-18511 A | 1/2004 |
| JP | 2004-521945 A | 7/2004 |
| JP | 2004-521946 A | 7/2004 |

*Primary Examiner*—Samuel Barts
(74) *Attorney, Agent, or Firm*—Birch, Stewart, Kolasch & Birch, LLP

(57) ABSTRACT

A sulfide chain-bearing organosilicon compound having the average compositional formula:

$$(R^1O)_{(3-p)}(R^2)_p Si-R^3-S-(R^4-S_m)_q-R^4-S-R^3-Si(OR^1)_{(3-p)}(R^2)_p$$

is prepared at low costs and in high yields by reacting a halogen-terminated organosilicon compound having the formula: $(R^1O)_{(3-p)}(R^2)_p Si-R^3-S-R^4-X$, sulfur, and optionally a halide having the formula: $X-R^4-X$ with an aqueous solution or dispersion of a sulfide $M_2S$ or hydrate thereof in the presence of a phase transfer catalyst. $R^1$ and $R^2$ are monovalent $C_{1-4}$ hydrocarbon groups, $R^3$ and $R^4$ are divalent $C_{1-10}$ hydrocarbon groups, m has an average value of 2-6, p is 0, 1 or 2, q is 1, 2 or 3, X is halogen, and M is ammonium or alkali metal.

3 Claims, No Drawings

PREPARATION OF SULFIDE CHAIN-BEARING ORGANOSILICON COMPOUNDS

CROSS-REFERENCE TO RELATED APPLICATION

This non-provisional application claims priority under 35 U.S.C. §119(a) on Patent Application No. 2005-285848 filed in Japan on Sep. 30, 2005, the entire contents of which are hereby incorporated by reference.

FIELD OF THE INVENTION

This invention relates to a sulfide chain-bearing organosilicon compound having an organoxysilyl group at each end and a polysulfide group at a center of the molecule, which are linked through a monosulfide-containing divalent hydrocarbon group. More particularly, it relates to a simple and economical method for preparing the sulfide chain-bearing organosilicon compound in an aqueous system using a phase transfer catalyst.

BACKGROUND ART

Compounds containing alkoxysilyl and polysulfide groups in the molecule are known. These compounds are utilized as interfacial binders between inorganic materials such as silica, aluminum hydroxide, talc and clay and organic materials such as thermoplastic resins, thermosetting resins and rubber, bonding agents for improving the adhesion of rubber to inorganic substrates, primers and the like.

Also known are various rubber compositions having silica loaded therein. Typical are tire tread-forming rubber compositions characterized by low heat generation and abrasion resistance. It is known in the art that compounds containing alkoxysilyl and polysulfide groups in the molecule, for example, bis-triethoxysilylpropyl tetrasulfide and bis-triethoxysilylpropyl disulfide are effective to compositions of this type. The inclusion of these compounds, however, is still insufficient to meet the requirements to further improve tensile strength, resilience and low heat generation.

One approach to improve the requisite properties is found in JP-A 2004-018511 (US Application Publication 2003/0236424 or EP 1375504A1) disclosing a compound having the average compositional formula (5):

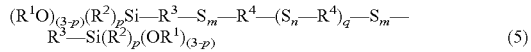
(5)

wherein each of $R^1$ and $R^2$ is a monovalent hydrocarbon group of 1 to 4 carbon atoms, each of $R^3$ and $R^4$ is a divalent hydrocarbon group of 1 to 15 carbon atoms, m is a positive number having an average value of 1 to 3, n is a positive number having an average value of 2 to 4, p is 0, 1 or 2, and q is 1, 2 or 3.

As disclosed therein, the organosilicon compound of the average compositional formula (5) is prepared by reacting a halogen-terminated organosilicon compound of the general formula (6):

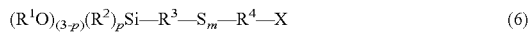
(6)

wherein $R^1$, $R^2$, $R^3$, $R^4$, m and p are as defined above, X is a halogen atom, with an anhydrous alkali metal sulfide or anhydrous alkali metal polysulfide of the general formula (7):

(7)

wherein M is an alkali metal and r is a positive number of 1 to 4 on average, and optionally a halogen-containing compound of the general formula (8):

(8)

wherein $R^4$ and X are as defined above and/or sulfur.

This method, however, has some drawbacks. While it uses substantially completely anhydrous alkali metal sulfide or alkali metal polysulfide, the drying of alkali metal sulfide or alkali metal polysulfide hydrate is time consuming. Filtration of the salt is necessary. Since the method normally uses a reaction solvent, the solvent must be distilled off at the end of reaction. There remains a need for a method for the preparation of sulfide chain-bearing organosilicon compounds in a simple step and at a low cost.

For the preparation of sulfide chain-bearing organosilicon compounds, the use of phase transfer catalysts is also known. This is taught in U.S. Pat. No. 5,405,985, U.S. Pat. No. 5,468,893, U.S. Pat. No. 5,583,245, U.S. Pat. No. 6,448,426, JP-A 2004-521945 and JP-A 2004-521946. Although these patents relate to methods for preparing sulfide chain-bearing organosilicon compounds using phase transfer catalysts, no reference is made to a sulfide chain-bearing organosilicon compound having an organoxysilyl group at each end and a polysulfide group at a center of the molecule, which are linked through a monosulfide-containing divalent hydrocarbon group.

SUMMARY OF THE INVENTION

An object of the present invention is to provide a safe and economical method for preparing in a simple step a sulfide chain-bearing organosilicon compound which is compounded in rubber for improving the tensile strength, resilience and low heat generation of rubber.

The inventors have discovered that a sulfide chain-bearing organosilicon compound having the average compositional formula (4):

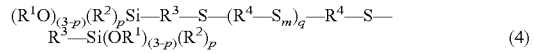
(4)

can be prepared by reacting a halogen-terminated organosilicon compound having the general formula (1):

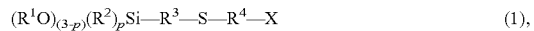
(1), sulfur, and optionally a halogen-containing compound having the general formula (2):

(2)

with an aqueous solution or dispersion of a sulfide having the formula (3):

(3)

or a hydrate thereof in the presence of a phase transfer catalyst. In the formulae, each of $R^1$ and $R^2$ is a monovalent hydrocarbon group of 1 to 4 carbon atoms, each of $R^3$ and $R^4$ is a divalent hydrocarbon group of 1 to 10 carbon atoms, m is a positive number having an average value of 2 to 6, p is 0, 1 or 2, and q is 1, 2 or 3, X is a halogen atom, and M is ammonium or alkali metal. This method is successful in preparing the compound of formula (4) in a simple and safe way, at low costs and in high yields because it eliminates a need for drying the sulfide or hydrate thereof as the raw material, and uses it in an aqueous solution or dispersion form.

Accordingly, the present invention provides a method for preparing a sulfide chain-bearing organosilicon compound having the average compositional formula (4), comprising the step of reacting a halogen-terminated organosilicon compound having formula (1), sulfur, and optionally a halogen-containing compound having formula (2) with an aqueous solution or dispersion of a sulfide having formula (3) or a hydrate thereof in the presence of a phase transfer catalyst.

BENEFITS OF THE INVENTION

According to the method of the invention, a sulfide chain-bearing organosilicon compound having the average compositional formula (4) can be prepared from a halogen-terminated organosilicon compound and a sulfide or hydrate thereof in the presence of a phase transfer catalyst without a need for drying the sulfide or hydrate thereof. The desired product is obtained in high yields and at low costs. The sulfide chain-bearing organosilicon compound thus prepared, when compounded in silica-loaded rubber, is effective for improving the tensile strength, resilience and low heat generation of the rubber, as compared with the prior art known sulfide chain-bearing organosilicon compounds. It is useful in the industry as an additive to silica-loaded tire rubber compositions.

DESCRIPTION OF THE PREFERRED EMBODIMENTS

Briefly stated, according to the present invention, a sulfide chain-bearing organosilicon compound having the average compositional formula (4) is obtained by reacting a halogen-terminated organosilicon compound having formula (1), sulfur, and optionally a halogen-containing compound having formula (2) with an aqueous solution or dispersion of a sulfide having formula (3) or a hydrate thereof in the presence of a phase transfer catalyst.

One starting reactant is a halogen-terminated organosilicon compound having the general formula (1).

$$(R^1O)_{(3-p)}(R^2)_p Si—R^3—S—R^4—X \qquad (1)$$

In the formula, $R^1$ and $R^2$ are independently selected from monovalent hydrocarbon groups having 1 to 4 carbon atoms, for example, alkyl and alkenyl groups such as methyl, ethyl, n-propyl, i-propyl, n-butyl, i-butyl, t-butyl, allyl and methallyl, with methyl and ethyl being preferred. $R^3$ is selected from divalent hydrocarbon groups having 1 to 10 carbon atoms, for example, alkylene, arylene and alkenylene groups and combinations thereof, such as methylene, ethylene, propylene, n-butylene, i-butylene, hexylene, decylene, phenylene, and methylphenylethylene, and combinations thereof. Of these, ethylene, propylene and i-butylene are preferred, with propylene being most preferred. $R^4$ is selected from divalent hydrocarbon groups having 1 to 10 carbon atoms, for example, alkylene, arylene and alkenylene groups and combinations thereof, such as methylene, ethylene, propylene, n-butylene, i-butylene, hexylene, decylene, phenylene, and methylphenylethylene, and combinations thereof. Of these, propylene, hexylene and decylene are preferred, with hexylene being most preferred. X is a halogen atom such as Cl, Br or I, and preferably Cl or Br. The subscript p is equal to 0, 1 or 2, preferably 0 or 1, and most preferably 0.

Typical examples of the compound of formula (1) are given below.

$(CH_3O)_3Si—(CH_2)_3—S—(CH_2)_3—Cl$ $(CH_3O)_3Si—(CH_2)_3—S—(CH_2)_6—Cl$ $(CH_3O)_3Si—(CH_2)_3—S—(CH_2)_8—Cl$ $(CH_3O)_3Si—(CH_2)_3—S—(CH_2)_{10}—Cl$ $(CH_3O)_3Si—(CH_2)_3—S—(CH_2)_6—Br$ $(CH_3CH_2O)_3Si—(CH_2)_3—S—(CH_2)_3—Cl$ $(CH_3CH_2O)_3Si—(CH_2)_3—S—(CH_2)_6—Cl$ $(CH_3CH_2O)_3Si—(CH_2)_3—S—(CH_2)_8—Cl$ $(CH_3CH_2O)_3Si—(CH_2)_3—S—(CH_2)_{10}—Cl$ $(CH_3CH_2O)_3Si—(CH_2)_3—S—(CH_2)_6—Br$ $(CH_3CH_2O)_3Si—CH_2CH(CH_3)CH_2—S—(CH_2)_6—Cl$

The phase transfer catalyst used herein is selected from quaternary onium cations. Examples of suitable quaternary onium cations include, but are not limited to, tetrabutylammonium bromide, tetrabutylammonium chloride, tetramethylammonium bromide, tetramethylammonium chloride, tetraethylammonium bromide, tetraethylammonium chloride, tetrabutylammonium phosphate, tetrabutylammonium phosphite, tetrabutylammonium sulfate, tetrabutylammonium fluoride, benzyltrimethylammonium bromide, and tetraphenylammonium bromide. Of these, tetra-n-butylammonium bromide and tetra-n-butylammonium chloride are preferred.

The sulfide has the formula (3):

$$M_2S \qquad (3)$$

wherein M is ammonium or an alkali metal. Non-limiting examples of M include Na, K, Cs, Li and $NH_4$, with Na being preferred. Examples of the sulfide $M_2S$ include $Na_2S$, $K_2S$, $Cs_2S$, $Li_2S$, and $(NH_4)_2S$, with $Na_2S$ being preferred. The sulfide may also take the form of a hydrate, for example, $Na_2S.6H_2O$ and $Na_2S.9H_2O$.

Optionally a halogen-containing compound having the general formula (2) is used in admixture with the organosilicon compound of formula (1).

$$X—R^4—X \qquad (2)$$

In formula (2), $R^4$ is a divalent hydrocarbon group of 1 to 10 carbon atoms. Examples of $R^4$ include alkylene, arylene and alkenylene groups and combinations thereof, such as methylene, ethylene, propylene, n-butylene, i-butylene, hexylene, decylene, phenylene, and methylphenylethylene, and combinations thereof. Of these, propylene, hexylene and decylene are preferred, with hexylene being most preferred. X is a halogen atom such as Cl, Br or I.

Typical examples of the compound of formula (2) are given below.

$Cl—(CH_2)_3—Cl$ $Cl—(CH_2)_6—Cl$ $Cl—(CH_2)_{10}—Cl$ $Br—(CH_2)_6—Br$ $Br—(CH_2)_{10}—Br$

In the method of the present invention, a halogen-terminated organosilicon compound having formula (1), sulfur, and optionally a halogen-containing compound having formula (2) are reacted with an aqueous solution or dispersion of a sulfide having formula (3) or a hydrate thereof in the presence of a phase transfer catalyst. One preferred procedure of performing this reaction involves mixing the halogen-terminated organosilicon compound having formula (1), sulfur, an aqueous solution or dispersion of the phase transfer catalyst and optionally the halogen-containing compound having formula (2) and then adding an aqueous solution or dispersion of the sulfide having formula (3) or a hydrate thereof to the mixture for reaction. This procedure allows for efficient production of the desired product, sulfide chain-bearing organosilicon compound having the average compositional formula (4).

Although the phase transfer catalyst is used in any desired amount, it may be added in an amount of 0.1 to 10% by weight, preferably 0.5 to 5.0% by weight, and more preferably 1.0 to 3.0% by weight, based on the weight of the compound of formula (1). Outside the range, less amounts of the catalyst may not be effective for the reaction to proceed rapidly whereas too much amounts of the catalyst may adversely affect the performance of the resultant organosilicon compound as a silica-loaded rubber additive.

The phase transfer catalyst may be premixed either with the compound of formula (1) and sulfur or with an aqueous solution or dispersion of the sulfide of formula (3) or hydrate thereof. The premixing with the compound of formula (1) is preferred because of quicker start of reaction.

When the phase transfer catalyst is mixed with the compound of formula (1) and sulfur, the phase transfer catalyst may be diluted with water. For dilution, the amount of water added may be 0 to about 500% by weight, preferably about 100 to about 300% by weight based on the weight of the phase transfer catalyst. When water is added, it is acceptable to mix the compound of formula (1) and sulfur with the phase transfer catalyst and then add water to the mixture. In this embodiment, the amount of water added is the same as above.

The sulfide of formula (3) or hydrate thereof is used in aqueous solution or water dispersion form. Although the amount of water added to the sulfide is not critical, water is preferably added in such amounts that a total amount of water is 10 to 1000% by weight, more preferably 30 to 300% by weight relative to the compound of formula (1) to be reacted with the sulfide of formula (3). Outside the range, smaller amounts of water may allow the sulfide or hydrate thereof to precipitate, with the concomitant difficulty of dispersion, and larger amounts of water may enhance the susceptibility of the compound of formula (1) to hydrolysis.

An aqueous solution or dispersion of the sulfide of formula (3) or hydrate thereof may be prepared by using hydrous sodium sulfide, the reaction product of hydrogen sulfide with alkali metal alcoholate, or the reaction product of metallic sodium or potassium with sulfur, and adding any of these sulfides or hydrates thereof to water.

With respect to the molar ratio of the compound of formula (1) to the sulfide of formula (3), it is a general practice to add the sulfide in accordance with the desired value of m in the average compositional formula (4) and use the compound of formula (1) in an equimolar amount to the M (ammonium or alkali metal) of the sulfide. It is understood that the system becomes alkaline as the moles of the compound of formula (1) is reduced, and becomes nearly neutral as the moles of the compound of formula (1) is increased. Specifically, the molar ratio of the compound of formula (1) to the sulfide of formula (3) is preferably from 1.9 to 2.2, more preferably from 2.0 to 2.1.

The amount of sulfur added is determined so as to provide the desired value of m in the average compositional formula (4) and is to make up the shortage of sulfur if observed after the charge of the sulfide of formula (3). The molar ratio of sulfur to the sulfide of formula (3) is preferably from 1.0 to 5.0, more preferably from 1.0 to 3.0, most preferably from 1.0 to 2.0. In one specific example where 2 mol of the compound of formula (1) is reacted with 1 mol of the sulfide $M_2S$ and 3 mol of sulfur, the resulting compound has the average compositional formula (4) wherein m has an average value of 4. In another specific example where 2 mol of the compound of formula (1) is reacted with 1 mol of the sulfide $M_2S$ and 1 mol of sulfur, the resulting compound has the average compositional formula (4) wherein m has an average value of 2.

In an optional embodiment wherein the compound of formula (2) is added, further amounts of the sulfide of formula (3) and sulfur may be added in accordance with the amount of the compound of formula (2) added. That is, the compounds of formulae (1) and (2) may be added in such amounts that the total moles of the compounds of formulae (1) and (2) is essentially equimolar to the M of the sulfide of formula (3): $M_2S$. Specifically, the molar ratio of the compounds of formulae (1) and (2) to the sulfide of formula (3) is preferably from 1.9 to 2.2, more preferably from 2.0 to 2.1.

With respect to the molar ratio of the compound of formula (1) to the compound of formula (2), 2 mol of the compound of formula (1) may be combined with 1 mol of the compound of formula (2) in order that q have an average value of 2, for example.

In preparing the compound of the invention, an organic solvent may or may not be used. While a solventless system is preferred, it is acceptable to use a solvent having low water solubility. For example, use may be made of aliphatic hydrocarbons such as pentane, hexane, heptane and octane and aromatic hydrocarbons such as benzene, toluene and xylene. When used, the amount of the solvent is not particularly limited, but is preferably up to about 2 times the amount of the compound of formula (1) and more preferably equal to or less than the amount of the compound of formula (1).

Although the reaction temperature is not critical, it is generally from room temperature to about 200° C., preferably about 40 to about 170° C., more preferably about 50 to about 100° C. The reaction time is generally 30 minutes or more, and the reaction proceeds to completion within about 1 hour to about 15 hours.

At the end of reaction, the reaction mixture is subjected to separatory operation so that it is separated into the desired compound layer and the water layer. If a salt has precipitated in the reaction mixture, water may be added to dissolve the salt, or filtration be made before and/or after the separation. Where a solvent is used, it may be distilled off in a partial vacuum after the separation.

To remove water from the desired compound, water may be distilled off in a partial vacuum after the separation. Alternatively, after the water layer is separated off, a desiccant is added to the desired compound for drying. Exemplary desiccants are sodium sulfate and magnesium sulfate.

The desired compound that is prepared by the inventive method has the average compositional formula (4).

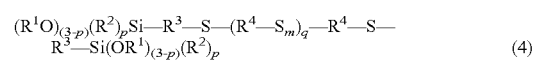

(4)

In the formula, $R^1$ and $R^2$ each are a monovalent hydrocarbon group of 1 to 4 carbon atoms, $R^3$ and $R^4$ each are a divalent hydrocarbon group of 1 to 10 carbon atoms, m is a positive number having an average value of 2 to 6, p is 0, 1 or 2, and q is 1, 2 or 3, preferably 1 or 2. $R^1$ to $R^4$ are as exemplified above for formula (1). The subscript m is a positive number having an average value of 2 to 6, preferably 2 to 4, more preferably 2 to 3.

Typical examples of the compound of formula (4) are given below wherein m and q are numbers having average values as described above.

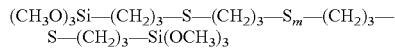

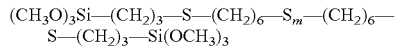

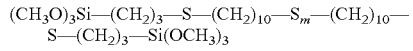

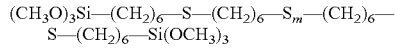

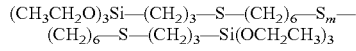

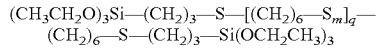

The sulfide chain-bearing organosilicon compounds of the average compositional formula (4) obtained by the method of the invention find use as rubber compounding additives, especially in silica-loaded rubber compositions for tire and similar applications.

EXAMPLE

Examples of the invention are given below by way of illustration and not by way of limitation.

Example 1

A 1-liter separable flask equipped with a nitrogen gas inlet, thermometer, Dimroth condenser and dropping funnel was charged with 142.6 g (0.4 mol) of 6-chlorohexylthiopropyl-triethoxysilane and 19.2 g (0.6 mol) of sulfur and heated at 80° C. To the flask was added an aqueous solution of 2.1 g of tetra-n-butylammonium bromide in 6.0 g of deionized water. Then an aqueous solution of 26.0 g (0.2 mol) of flake sodium sulfide having a sodium sulfide content of 59 wt % in 200 g of deionized water was slowly added dropwise so as to keep a temperature of 80-90° C. The time taken for dropwise addition was 20 minutes. After the completion of dropwise addition, the reaction mixture was held for 5 hours for ripening. Thereafter, the reaction mixture was cooled below 40° C., combined with 100 g of toluene, and filtered. The reaction liquid as filtered separated into upper and lower layers. The lower layer was an aqueous solution in which NaCl formed was dissolved. The upper layer was concentrated under a partial vacuum to remove the toluene, leaving 148.0 g of a red brown clear liquid. The liquid had a viscosity of 50.8 mm$^2$/s, a refractive index of 1.5073, and a specific gravity of 1.072 at 25° C.

On analysis by infrared (IR) absorption spectroscopy, proton nuclear magnetic resonance ($^1$H-NMR) spectroscopy, gel permeation chromatography (GPC), supercritical chromatography, and sulfur content determination, it was confirmed to be a sulfide group-bearing alkoxysilane of the following average compositional formula.

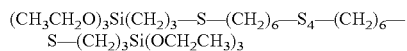

Example 2

A 1-liter separable flask equipped with a nitrogen gas inlet, thermometer, Dimroth condenser and dropping funnel was charged with 142.6 g (0.4 mol) of 6-chlorohexylthiopropyl-triethoxysilane and 9.6 g (0.3 mol) of sulfur and heated at 80° C. To the flask was added an aqueous solution of 2.1 g of tetra-n-butylammonium bromide in 6.0 g of deionized water. Then an aqueous solution of 26.0 g (0.2 mol) of flake sodium sulfide having a sodium sulfide content of 59 wt % in 200 g of deionized water was slowly added dropwise so as to keep a temperature of 80-90° C. The time taken for dropwise addition was 20 minutes. After the completion of dropwise addition, the reaction mixture was held for 5 hours for ripening. Thereafter, the reaction mixture was cooled below 40° C., combined with 100 g of toluene, and filtered. The reaction liquid as filtered separated into upper and lower layers. The lower layer was an aqueous solution in which NaCl formed was dissolved. The upper layer was concentrated under a partial vacuum to remove the toluene, leaving 135.0 g of a red brown clear liquid. The liquid had a viscosity of 45.9 mm$^2$/s, a refractive index of 1.4908, and a specific gravity of 1.044 at 25° C.

On analysis by IR spectroscopy, $^1$H-NMR spectroscopy, GPC, supercritical chromatography, and sulfur content determination, it was confirmed to be a sulfide group-bearing alkoxysilane of the following average compositional formula.

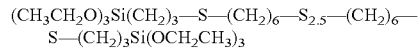

Example 3

A 1-liter separable flask equipped with a nitrogen gas inlet, thermometer, Dimroth condenser and dropping funnel was charged with 142.6 g (0.4 mol) of 6-chlorohexylthiopropyl-triethoxysilane, 31.0 g (0.2 mol) of 1,6-dichlorohexane, and 38.4 g (1.2 mol) of sulfur and heated at 80° C. To the flask was added an aqueous solution of 4.2 g of tetra-n-butyl-ammonium bromide in 10.0 g of deionized water. Then an aqueous solution of 52.0 g (0.4 mol) of flake sodium sulfide having a sodium sulfide content of 59 wt % in 200 g of deionized water was slowly added dropwise so as to keep a temperature of 80-90° C. The time taken for dropwise addition was 20 minutes. After the completion of dropwise addition, the reaction mixture was held for 5 hours for ripening. Thereafter, the reaction mixture was cooled below 40° C., combined with 200 g of toluene, and filtered. The reaction liquid as filtered separated into upper and lower layers. The lower layer was an aqueous solution in which NaCl formed was dissolved. The upper layer was concentrated under a partial vacuum to remove the toluene, leaving 167.0 g of a red brown clear liquid. The liquid had a viscosity of 146 mm$^2$/s, a refractive index of 1.5360, and a specific gravity of 1.112 at 25° C.

On analysis by IR spectroscopy, $^1$H-NMR spectroscopy, GPC, supercritical chromatography, and sulfur content determination, it was confirmed to be a sulfide group-bearing alkoxysilane of the following average compositional formula.

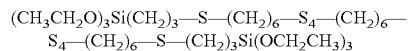

Example 4

A 1-liter separable flask equipped with a nitrogen gas inlet, thermometer, Dimroth condenser and dropping funnel was charged with 142.6 g (0.4 mol) of 6-chlorohexylthiopropyl-triethoxysilane, 31.0 g (0.2 mol) of 1,6-dichlorohexane, and 19.2 g (0.6 mol) of sulfur and heated at 80° C. To the flask was added an aqueous solution of 4.2 g of tetra-n-butyl-ammonium bromide in 10.0 g of deionized water. Then an aqueous solution of 52.0 g (0.4 mol) of flake sodium sulfide having a sodium sulfide content of 59 wt % in 200 g of deionized water was slowly added dropwise so as to keep a temperature of 80-90° C. The time taken for dropwise addition was 20 minutes. After the completion of dropwise addition, the reaction mixture was held for 5 hours for ripening. Thereafter, the reaction mixture was cooled below 40° C., combined with 200 g of toluene, and filtered. The reaction liquid as filtered separated into upper and lower layers. The lower layer was an aqueous solution in which NaCl formed was dissolved. The upper layer was concentrated under a partial vacuum to remove the toluene, leaving 155.0 g of a red brown clear liquid. The liquid had a viscosity of 112 nmm²/s, a refractive index of 1.5117, and a specific gravity of 1.072 at 25° C.

On analysis by IR spectroscopy, ¹H-NMR spectroscopy, GPC, supercritical chromatography, and sulfur content determination, it was confirmed to be a sulfide group-bearing alkoxysilane of the following average compositional formula.

$$(CH_3CH_2O)_3Si(CH_2)_3\text{—}S\text{—}(CH_2)_6\text{—}S_{2.5}\text{—}(CH_2)_6\text{—}S_{2.5}\text{—}(CH_2)_6\text{—}S\text{—}(CH_2)_3Si(OCH_2CH_3)_3$$

Japanese Patent Application No. 2005-285848 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A method for preparing a sulfide chain-bearing organosilicon compound having the average compositional formula (4):

$$(R^1O)_{(3-p)}(R^2)_pSi\text{—}R^3\text{—}S\text{—}(R^4\text{—}S_m)_q\text{—}R^4\text{—}S\text{—}R^3\text{—}Si(OR^1)_{(3-p)}(R^2)_p \quad (4)$$

wherein $R^1$ and $R^2$ each are a monovalent hydrocarbon group of 1 to 4 carbon atoms, $R^3$ and $R^4$ each are a divalent hydrocarbon group of 1 to 10 carbon atoms, m is a positive number having an average value of 2 to 6, p is 0, 1 or 2, and q is 1, 2 or 3, the method comprising the step of reacting a halogen-terminated organosilicon compound having the general formula (1):

$$(R^1O)_{(3-p)}(R^2)_pSi\text{—}R^3\text{—}S\text{—}R^4\text{—}X \quad (1)$$

wherein $R^1$ and $R^2$ each are a monovalent hydrocarbon group of 1 to 4 carbon atoms, $R^3$ and $R^4$ each are a divalent hydrocarbon group of 1 to 10 carbon atoms, X is a halogen atom, and p is 0, 1 or 2, sulfur, and optionally a halogen-containing compound having the general formula (2):

$$X\text{—}R^4\text{—}X \quad (2)$$

wherein $R^4$ is a divalent hydrocarbon group of 1 to 10 carbon atoms and X is a halogen atom, with an aqueous solution or dispersion of a sulfide having the formula (3):

$$M_2S \quad (3)$$

wherein M is ammonium or an alkali metal or a hydrate thereof in the presence of a phase transfer catalyst.

2. The method of claim 1 wherein the halogen-terminated organosilicon compound of formula (1), sulfur, an aqueous solution or dispersion of the phase transfer catalyst, and optionally the halogen-containing compound of formula (2) are mixed prior to the reaction with an aqueous solution or dispersion of the sulfide of formula (3) or hydrate thereof.

3. The method of claim 1 wherein in the average compositional formula (4), m is a positive number having an average value of 2 to 3.

* * * * *